(12) United States Patent
Robinson et al.

(10) Patent No.: US 9,519,215 B2
(45) Date of Patent: Dec. 13, 2016

(54) COMPOSITION OF MATTER AND MOLECULAR RESIST MADE THEREFROM

(71) Applicants: Alex Phillip Graham Robinson, Birmingham (GB); Dongxu Yang, Selly Oak Birmingham (GB); Andreas Frommhold, Anger (DE); Thomas Lada, Somerville, MA (US); John L. Roth, Cohasset, MA (US); Xiang Xue, Winchester, MA (US); Edward A. Jackson, Franklin, MA (US)

(72) Inventors: Alex Phillip Graham Robinson, Birmingham (GB); Dongxu Yang, Selly Oak Birmingham (GB); Andreas Frommhold, Anger (DE); Thomas Lada, Somerville, MA (US); John L. Roth, Cohasset, MA (US); Xiang Xue, Winchester, MA (US); Edward A. Jackson, Franklin, MA (US)

(73) Assignee: IRRESISTIBLE MATERIALS, LTD, Swansea, Wiles (GB)

( * ) Notice: Subject to any disclaimer, the term of this patent is extended or adjusted under 35 U.S.C. 154(b) by 0 days.

(21) Appl. No.: 14/977,520

(22) Filed: Dec. 21, 2015

(65) Prior Publication Data
US 2016/0246173 A1   Aug. 25, 2016

Related U.S. Application Data

(63) Continuation-in-part of application No. 14/520,037, filed on Oct. 21, 2014, now Pat. No. 9,229,322, which
(Continued)

(51) Int. Cl.
G03F 7/004 (2006.01)
C07D 223/00 (2006.01)
(Continued)

(52) U.S. Cl.
CPC ........... G03F 7/0045 (2013.01); C07D 245/02 (2013.01); C07D 487/14 (2013.01); C07D 498/14 (2013.01);
(Continued)

(58) Field of Classification Search
CPC ........... G03F 7/0045; G03F 7/20; G03F 7/38; G03F 7/027; C07D 245/02; C07D 487/14; C07D 498/14; H01L 51/0047
(Continued)

(56) References Cited

U.S. PATENT DOCUMENTS 4,950,585 A * 8/1990 Tachibana ............ G03C 7/3825
                                                        430/384
7,838,438 B2 * 11/2010 Im ........................ C23C 16/40
                                                      257/E21.282
(Continued)

*Primary Examiner* — Amanda C Walke
(74) *Attorney, Agent, or Firm* — The Patent Practice of Szmanda & Shelnut, LLC.; Charles R. Szmanda; James G. Shelnut

(57) ABSTRACT

The present application for patent discloses a composition of matter comprising: comprising a solvent; and an ester having a chemical structure chosen from (I), (II), or (III);

(Continued)

-continued

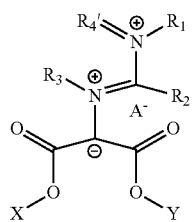
(II)

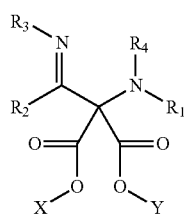

(III)

wherein X and Y are the same or different, wherein at least one of X and Y comprises an acid labile group, wherein $R_1$ is a saturated or unsaturated group having from 1-4 carbon atoms, $R_2$ is chosen from hydrogen or a saturated or unsaturated group having from 1-4 carbon atoms, $R_3$ is a saturated or unsaturated group having from 1-4 carbon atoms, and $R_4$ is a saturated or unsaturated group having from 1-4 carbon atoms and $A^-$ is an anion.

20 Claims, 4 Drawing Sheets

Related U.S. Application Data is a continuation-in-part of application No. 14/068,254, filed on Oct. 31, 2013, now Pat. No. 9,256,126.

(51) Int. Cl.
*C07D 245/02* (2006.01)
*C07D 487/14* (2006.01)
*C07D 498/14* (2006.01)
*G03F 7/027* (2006.01)
*H01L 51/00* (2006.01)
*G03F 7/38* (2006.01)

(52) U.S. Cl.
CPC ............. *G03F 7/027* (2013.01); *G03F 7/38* (2013.01); *H01L 51/0047* (2013.01)

(58) Field of Classification Search
USPC ...... 430/270.1; 540/470, 484, 578, 579, 567
See application file for complete search history.

(56) References Cited

U.S. PATENT DOCUMENTS

| | | | |
|---|---|---|---|
| 8,062,429 B2* | 11/2011 | Lee | C11D 7/3263 134/1.3 |
| 8,173,584 B2* | 5/2012 | Lee | G03F 7/426 134/1.3 |
| 2010/0105595 A1* | 4/2010 | Lee | C09G 1/02 510/176 |

* cited by examiner

COMPOSITION OF MATTER AND MOLECULAR RESIST MADE THEREFROM

REFERENCE TO PRIOR FILED APPLICATIONS

The present application is a continuation-in-part, and claims the benefit under 35 U.S.C. §120, of U.S. patent application Ser. No. 14/520,037, filed on 21 Oct., 2014, entitled "Composition of Matter and Molecular Resist Made Therefrom," which is a continuation in part of U.S. patent application Ser. No. 14/068,254 filed on 14 Nov., 2012, entitled "Methanofullerenes," which applications are incorporated by reference herein in their entirety.

FIELD OF THE INVENTION

The present application for patent is in the field of nanolithography materials and more specifically is in the field of molecular glass resists.

BACKGROUND

As is well known, the manufacturing process of various kinds of electronic or semiconductor devices such as ICs, LSIs and the like involves fine patterning of a resist layer on the surface of a substrate material such as a semiconductor silicon wafer. This fine patterning process has traditionally been conducted by the photolithographic method in which the substrate surface is uniformly coated with a positive or negative tone photosensitive composition to form a thin layer and selectively irradiating with actinic rays (such as ultraviolet (UV), deep UV, vacuum UV, extreme UV, x-rays, electron beams and ion beams) via a transmission or reflecting mask followed by a development treatment to selectively dissolve away the coated photosensitive layer in the areas exposed or unexposed, respectively, to the actinic rays leaving a patterned resist layer on the substrate surface. The patterned resist layer, thus obtained, may be utilized as a mask in the subsequent treatment on the substrate surface such as etching. The fabrication of structure with dimensions of the order of nanometers is an area of considerable interest since it enables the realization of electronic and optical devices which exploit novel phenomena such as quantum confinement effects and also allows greater component packing density. As a result, the resist pattern is required to have an ever increasing fineness which can be accomplished by using actinic rays having a shorter wavelength than the conventional ultraviolet light. Accordingly, it is now the case that, in place of the conventional ultraviolet light, electron beams (e-beams), excimer laser beams, EUV, BEUV and X-rays are used as the short wavelength actinic rays. Needless to say the minimum size obtainable is, in part, determined by the performance of the resist material and, in part, the wavelength of the actinic rays. Various materials have been proposed as suitable resist materials. For example, in the case of negative tone resists based on polymer cross-linking, there is an inherent resolution limit of about 10 nm, which is the approximate radius of a single polymer molecule.

It is also known to apply a technique called "chemical amplification" to resist materials. A chemically amplified resist material is generally a multi-component formulation in which there is a matrix material, frequently a main polymeric component, such as a polyhydroxystyrene (PHOST) resin protected by acid labile groups and a photo acid generator (PAG), as well as one or more additional components which impart desired properties to the resist. The matrix material contributes toward properties such as etching resistance and mechanical stability. By definition, the chemical amplification occurs through a catalytic process involving the PAG, which results in a single irradiation event causing the transformation of multiple resist molecules. The acid produced by the PAG reacts catalytically with the polymer to cause it to lose a functional group or, alternatively, cause a crosslinking event. The speed of the reaction can be driven, for example, by heating the resist film. In this way the sensitivity of the material to actinic radiation is greatly increased, as small numbers of irradiation events give rise to a large number of solubility changing events. As noted above, chemically amplified resists may be either positive or negative working.

Certain chemically amplified resists do not use large polymers. In cases where nanometer-scale patterning is desired, low molecular weight polymers or even small molecules may be used as the resist matrix material. These are sometimes referred to as "molecular glass" resists (MGRs), taken in this instance to include molecules such as oligomers, polyaromatic hydrocarbon derivatives, discotic liquids crystals, fullerenes, macrocycles, small amorphous, and other low molecular weight resists. Although MGRs may offer many potential advantages over polymeric chemically amplified resists, there are still some things about this class of materials that could potentially pose challenges. Removal and subsequent volatilization of protecting groups in positive tone molecular resists may cause a loss of up to approximately 50% of the mass of the resist, potentially leading to a loss of pattern quality. The small sizes of molecular resist compounds, and often correspondingly low glass transition temperatures, can also restore material integrity but may compromise pattern quality.

Accordingly, there is a need for improved molecular glass resists. It is to the provision and characterization of such molecular glass resists that the various embodiments of the present written description are directed.

DETAILED DESCRIPTION OF THE DRAWINGS

Figure 1:
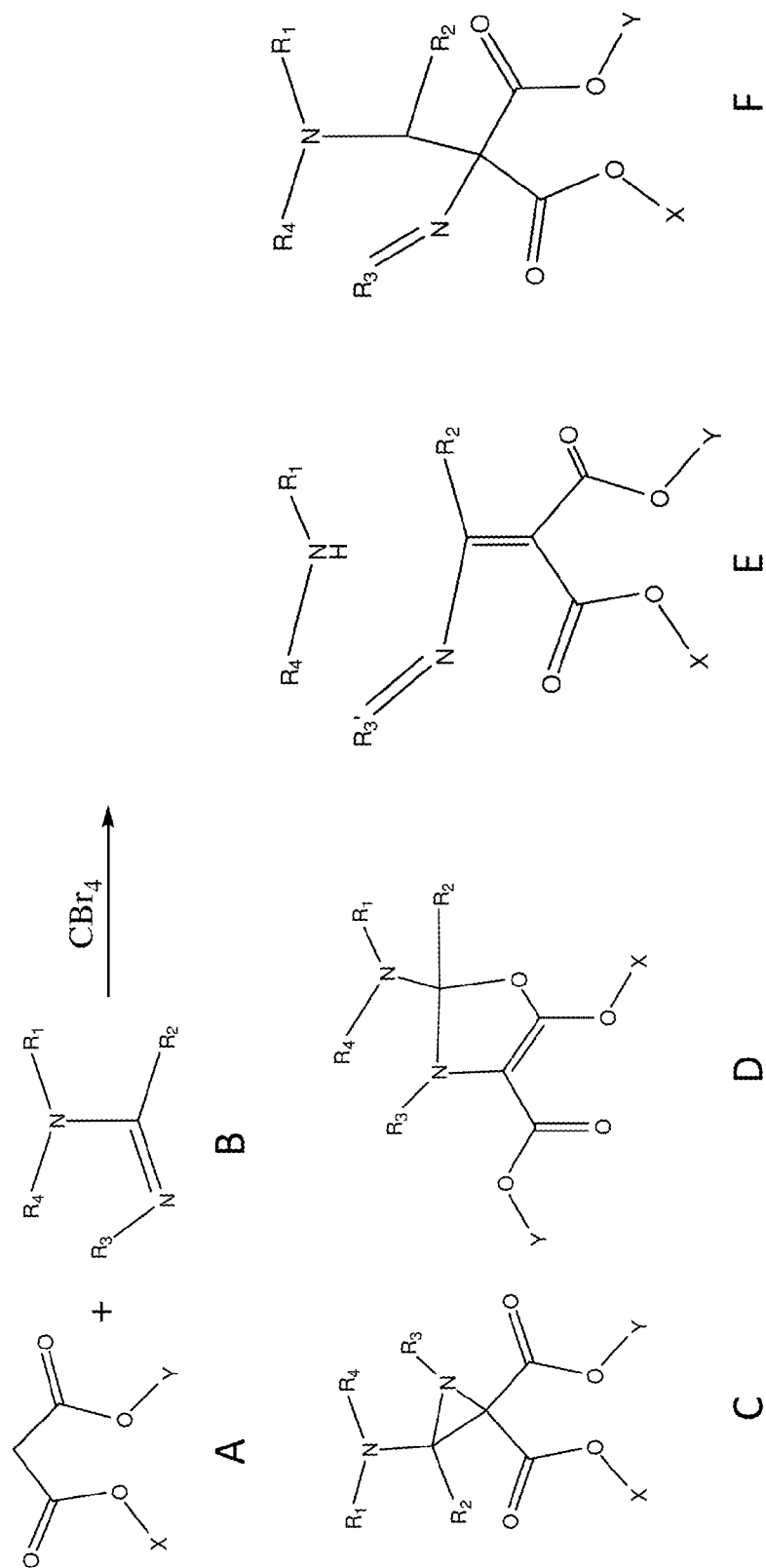
FIG. 1 illustrates the general reaction of an imidamide with a malonate ester in the presence of a bromine donor such as $CBr_4$ as disclosed herein.

FIG. 1 illustrates the general reaction of an imidamide with a malonate ester, in the presence of a bromine donor such as $CBr_4$ as disclosed herein. The malonate ester, A, reacts with the imidamide, B, in the presence of $CBr_4$ to yield possible products C, D, E and F that are believed to be energetically accessible under certain reaction conditions.

Figure 2:
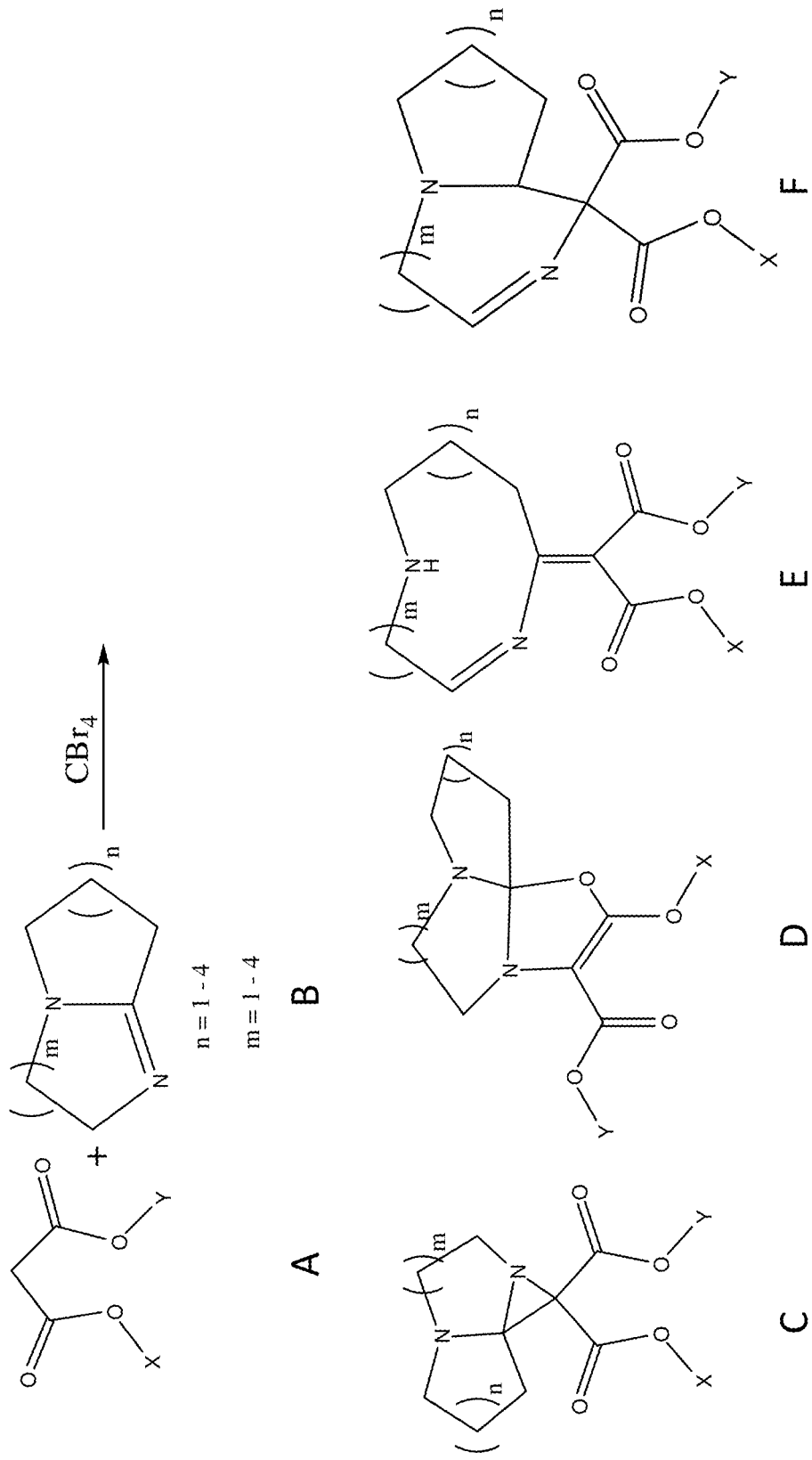
FIG. 2 illustrates the reaction of a fused ring imidamide with a malonate ester, in the presence of a bromine donor such as $CBr_4$ as disclosed herein.

FIG. 2 illustrates the general reaction of a fused ring imidamide with a malonate ester, in the presence of a bromine donor such as $CBr_4$ as disclosed herein. The malonate ester, A, reacts with the fused ring imidamide, B, in the presence of CBr₄ to yield possible products C, D, E and F that are believed to be energetically accessible under certain reaction conditions.

Figure 3:
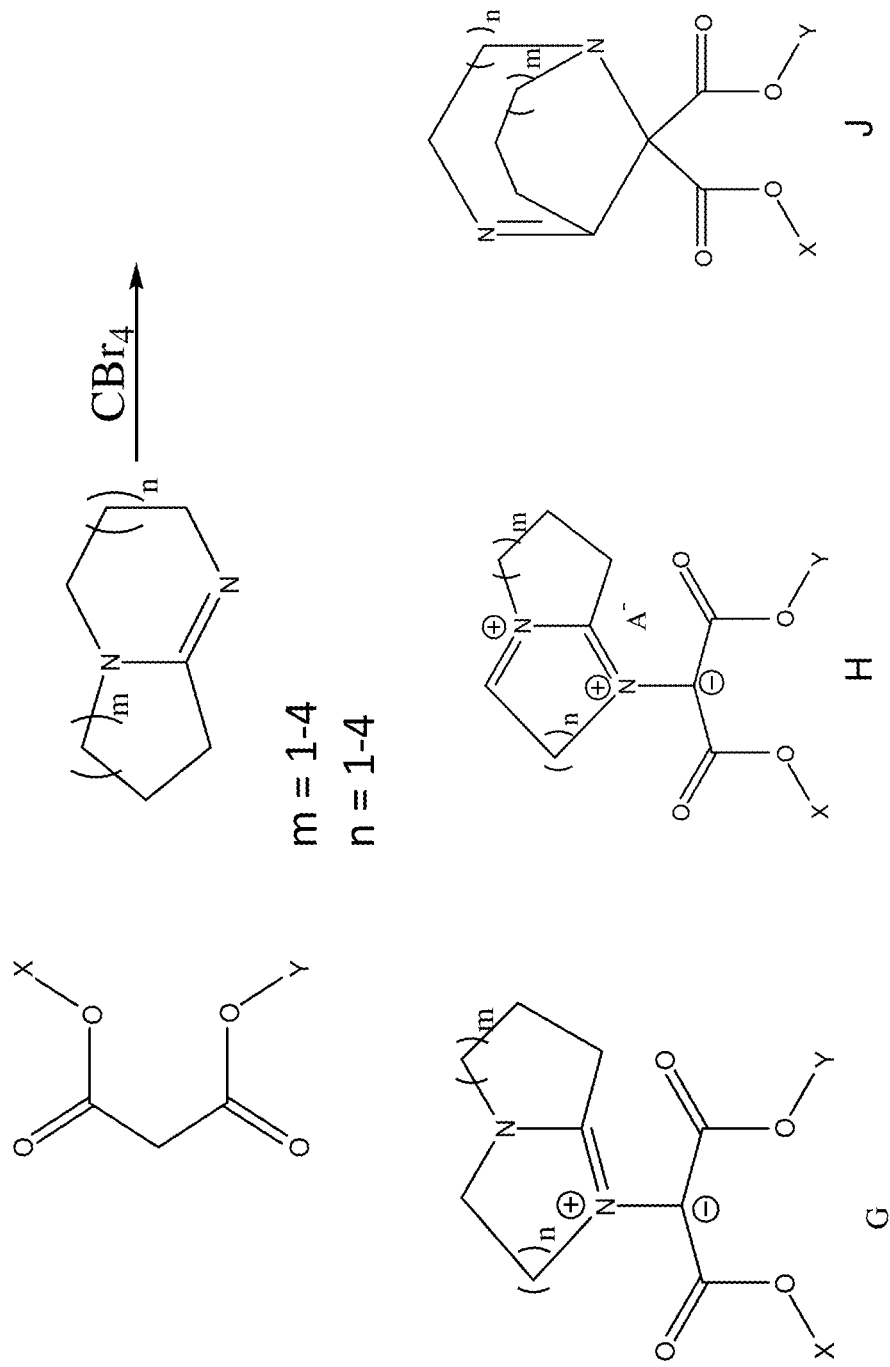
FIG. 3 illustrates the general reaction of a fused ring imidamide with a malonate ester, in the presence of a bromine donor such as $CBr_4$ as disclosed herein, yielding further products of reaction.

FIG. 3 illustrates further structures from the reaction of a fused ring imidamide with a malonate ester, in the presence of a bromine donor such as CBr₄ as disclosed herein, together with the products believed to be obtained therefrom. The malonate ester, A, reacts with the fused ring imidamide, B, in the presence of CBr₄ to yield products G, H, and J, believed to be energetically accessible under certain reaction conditions.

Figure 4:
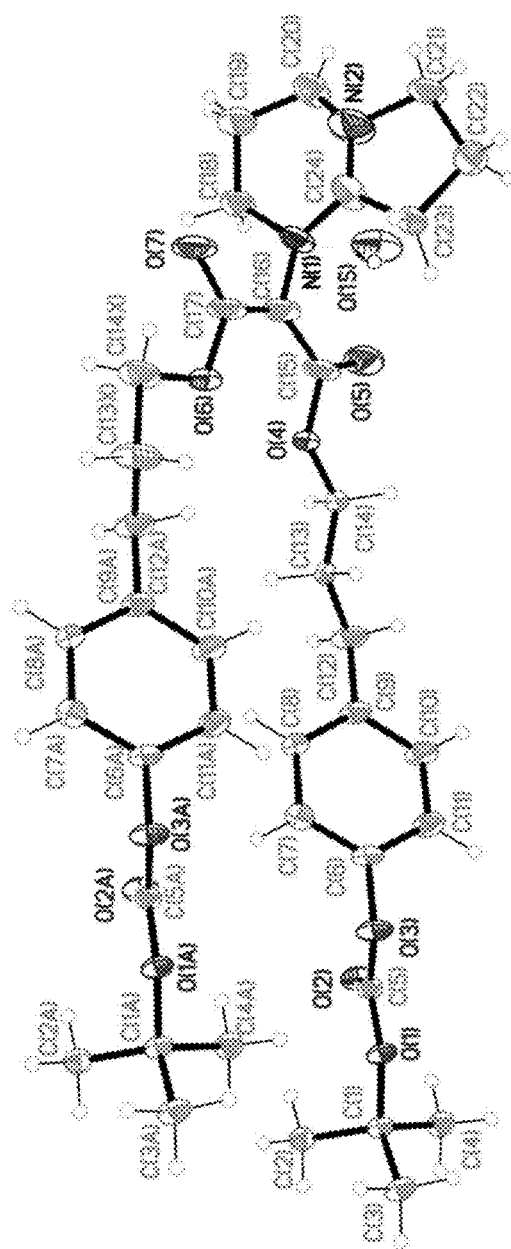
FIG. 4 shows the result of an X-ray single crystal structure determination.

FIG. 4 shows the result of an X-ray single crystal structure determination. The structure shown in the Figure appears to correspond to Structure H in FIG. 3.

DETAILED DESCRIPTION

As used herein, the conjunction "and" is intended to be inclusive and the conjunction "or" is not intended to be exclusive unless otherwise indicated or required by the context. For example, the phrase "or, alternatively" is intended to be exclusive. As used herein, the term "exemplary" is intended to describe an example and is not intended to indicate preference. As used herein, the term "energetically accessible" is used to describe products that may be thermodynamically or kinetically available via a chemical reaction.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise. Unless otherwise required by the context, chemical substitution material in parentheses indicates that the substitution may or may not be present. Thus, for example "(perfluoro)octanesulfinate" may or may not include perfluorination.

Disclosed herein is a composition of matter, comprising an ester, wherein the ester is product of a chemical reaction between a malonate ester and an imidamide in the presence of a suitable halogen donor or pseudohalogen donor.

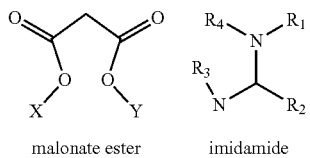

malonate ester     imidamide wherein X and Y are the same or different, wherein at least one of X and Y comprises a labile group, such as for instance an acid labile group, wherein R₁ is a saturated or unsaturated group having from 1-4 carbon atoms, R₂ is chosen from hydrogen or a saturated or unsaturated group having from 1-4 carbon atoms, R₃ is a saturated or unsaturated group having from 1-4 carbon atoms, and R₄ is a saturated or unsaturated group having from 1-4 carbon atoms.

Further disclosed herein is a composition of matter produced by the above chemical reaction wherein R₂ is a saturated or unsaturated group having from 1-4 carbon atoms, R₁ and R₂ are conjoined by a chemical bond to form a ring structure having 5-8 members, and wherein R₃ and R₄ are conjoined by a chemical bond to form a ring structure having 5-8 members.

Still further disclosed herein is a composition of matter, wherein the imidamide comprises a fused ring structure as shown:

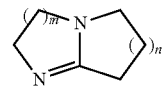

wherein m=1-4 and n=1-4.

Disclosed herein is a composition of matter comprising: an ester having a chemical structure chosen from (I), (II), (III), or (IV);

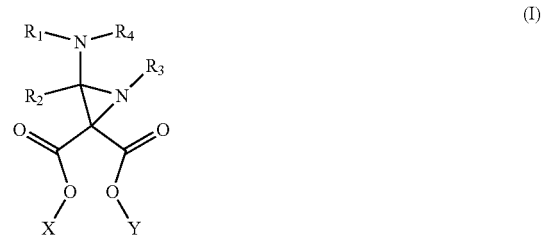

(I)

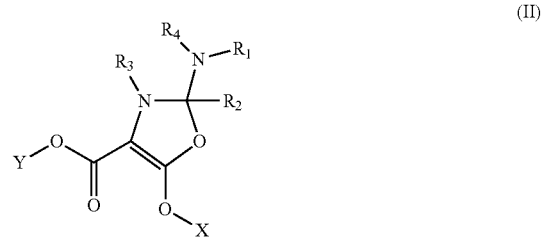

(II)

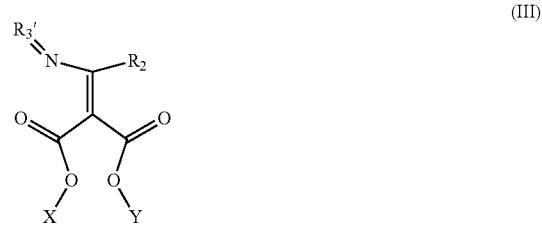

(III)

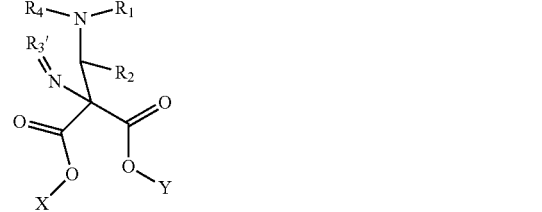

(IV)

wherein X and Y are the same or different, wherein at least one of X and Y comprises an acid labile group, wherein R1 is a saturated or unsaturated group having from 1-4 carbon atoms, R2 is chosen from hydrogen or a saturated or unsaturated group having from 1-4 carbon atoms, R3 is a saturated or unsaturated group having from 1-4 carbon atoms, and R4 is a saturated or unsaturated group having from 1-4 carbon atoms. In the above, the group —N=R₃' is used here to denote the ylidene amine, produced starting with the group R₃, where permitted by the chemical substitution.

Further disclosed herein is a composition of matter, described by (I)-(IV), wherein $R_2$ is a saturated or unsaturated group having from 1-4 carbon atoms, $R_1$ and $R_2$ are conjoined by a chemical bond to form a ring structure having 5-8 members, and wherein $R_3$ and $R_4$ are conjoined by a chemical bond to form a ring structure having 5-8 members, where appropriate.

Disclosed herein is a composition of matter having a structure chosen from (V), (VI), (VII), or (VIII), wherein X and Y are the same or different, and wherein at least one of X or Y comprises an acid labile group and wherein m=1-4 and wherein n=1-4.

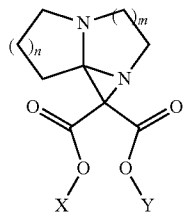

(V)

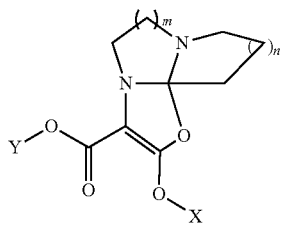

(VI)

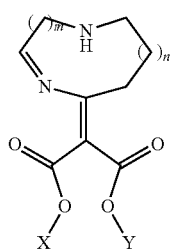

(VII)

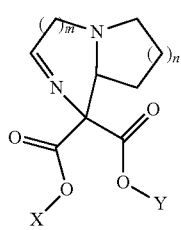

(VIII)

Disclosed herein is a composition of matter comprising: an ester having a chemical structure chosen from (V), (VI), (VII) or (VIII); wherein m=1-4, n=1-4, and wherein X and Y are the same or different, wherein at least one of X and Y comprises an acid labile group.

Further disclosed herein is a composition of matter comprising: comprising a solvent; and an ester having a chemical structure chosen from (IX), (X), or (XI);

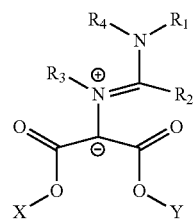

(IX)

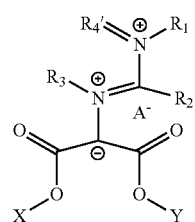

(X)

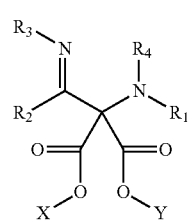

(XI)

wherein X and Y are the same or different, wherein at least one of X and Y comprises an acid labile group, wherein $R_1$ is a saturated or unsaturated group having from 1-4 carbon atoms, $R_2$ is chosen from hydrogen or a saturated or unsaturated group having from 1-4 carbon atoms, $R_3$ is a saturated or unsaturated group having from 1-4 carbon atoms, and $R_4$ is a saturated or unsaturated group having from 1-4 carbon atoms and $A^-$ is an anion.

Further disclosed herein is a composition of matter comprising: a solvent; and an ester having a chemical structure chosen from (XII), (XIII), or (XIV);

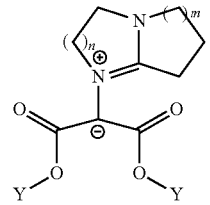

(XII)

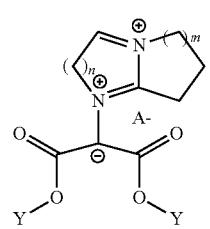

(XIII)

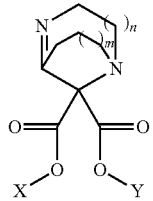

(XIV)

wherein m=1-4, n=1-4, and wherein X and Y are the same or different, wherein at least one of X and Y comprises an acid labile group and wherein A- is an anion.

In the above disclosed structures, it is also contemplated that tautomers and other resonance structures may also be energetically available. The structures, disclosed supra, are therefore intended to include tautomers and other resonance structures. For example:

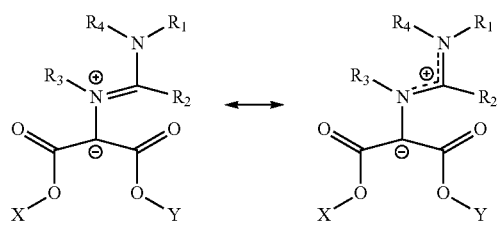

In the above disclosed structures, at least one of X or Y may comprise an acid labile group, such that X or Y has the general structure

-E-O$_p$-(COO)$_q$-LG which may or may not comprise an extender chain, -E-, wherein p and q may take the values in the following table such that when E is not present, the malonic carboxyl group forms the ester:

| (—E—) | (—O—) | (—COO—) |
|---|---|---|
| Present | p | q |
| Present | 1 | 1 |
| Present | 0 | 1 |
| Present | 1 | 0 |
| Not Present | 0 | 1 |

For example, the acid labile group may comprise a carbonate (for which p=1 and q=1), a carboxylate (for which p=0 and q=1), or a phenoxy ether (for which p=1 and q=0), and a leaving group, LG. In the case of the carbonate esters, both the leaving group and CO$_2$ are eliminated during the deprotection reaction, leaving behind an —OH group. In the case of the carboxylate esters and phenoxy ethers, the leaving group is eliminated, leaving behind a carboxylic acid or phenol, respectively. In certain circumstances, the carboxylic acid, produced by deprotection of the carboxylate ester may further be eliminated via decarboxylation using a base such as imidazole. As a further example, either or both of X and Y may comprise a structure such as

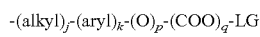

-(alkyl)$_j$-(aryl)$_k$-(O)$_p$-(COO)$_q$-LG wherein m, n, p, and q take values as shown in the following table:

| -alkyl- j | -aryl- k | —O— p | —COO— q |
|---|---|---|---|
| 1 | 1 | 1 | 1 |
| 1 | 1 | 0 | 1 |
| 1 | 1 | 1 | 0 |
| 1 | 0 | 0 | 1 |
| 1 | 0 | 1 | 0 |
| 0 | 1 | 1 | 1 |
| 0 | 1 | 0 | 1 |
| 0 | 1 | 1 | 0 |
| 0 | 0 | 0 | 1 | wherein, when a divalent moiety has a 0 subscript, the remaining groups connect, wherein alkyl is a branched or unbranched, substituted or unsubstituted divalent alkyl chain of 1-16 carbon atoms having 0-16 heteroatoms substituted into the chain, aryl is a substituted or unsubstituted divalent phenyl group, divalent heteroaromatic group, or divalent fused aromatic or fused heteroaromatic group, wherein —(O)$_p$—(COO)$_q$-LG is an acid labile group and wherein LG is a leaving group. In addition to the carbonate ester, depicted above, the acid labile group may comprise an acid labile carboxylic acid ester having similar leaving groups, LG. The acid labile group may be a tert-butyl carbonate group, a tert-butyl carboxylate group or other carbonate or carboxylate ester having a leaving group such as, without limitation, a tertiary alkyl or tertiary cycloalkyl group, an allicyclic group, a ketal or cyclic aliphatic ketal, or an acetal. In addition, the acid labile group may comprise a mass persistent moiety in which p=0 and the leaving group is bonded to the extender chain. Non limiting examples may generally be represented by the structure:

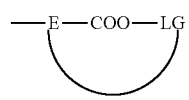

which may, for example, include the following:

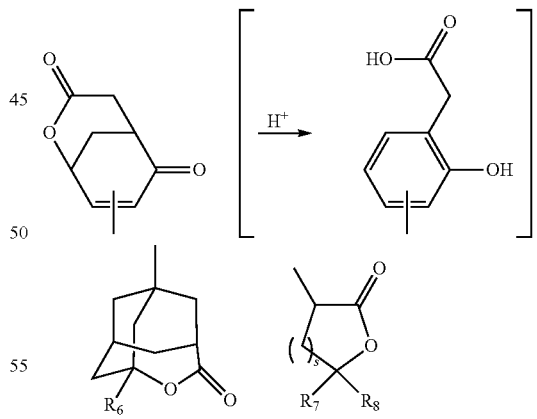

wherein the foregoing mater in brackets shows the acidolysis reaction, wherein the points of attachment to the remainder of the group, E, are shown. Wherein R$_6$ is a hydrogen, methyl, ethyl, or benzyl group, R$_7$ and R$_8$ may be the same or different and may be methyl, ethyl, or benzyl groups and s=0 to 4. Examples of mass persistent resists are known. See, for example, Klop et al., Chem. Commun., (2002), 2956-2957, and Ushirogouchi et al., Proc. SPIE, 3999, 1147, (2000).

In addition, X and Y may comprise, for example, without limitation, no extender chain, or divalent extender chains comprising -alkyl-, -aryl-, -alkyl-aryl-, -aryl-alkyl-, -alkoxy-, -alkoxy-aryl-, -aryl-alkoxy-, -alkyl-alkoxy-, -alkoxy-alkyl-, or combinations of the foregoing.

More specifically, the -alkyl-group, above, can be a branched or unbranched divalent alkyl chain of 1-16 carbons with or without heteroatoms substituted into the chain, such as, for example, —CH2-, -CH2CH2-, -CH(CH3)CH2-, -CH2CH2CH2-, -CH2CH2CH2CH2-, butylene isomers, and the higher analogs up to and including hexadecylene, as well as their isomers. As used herein -alkyl- also includes any unsaturations in the chain such an olefin group, such as for example, —CH=CH—, or an alkynyl group. As mentioned the -alkyl-group may have heteroatoms substituted into the chain as part or the chain, such as O, N, S, S=O or SO2 and the like, such as, for example, -(CH2CH2-O)$_z$- wherein z is between about 1 and about 16, or -(CH2CH2NH)$_w$- wherein w is between about 1 and about 16, and the like. In accordance with the description above, the group, -alkoxy- may comprise one or more branched or unbranched alkyl groups such as -ethoxy-, -propoxy- or -isopropoxy-groups, separated by oxygen atoms. Also included are branched alkyl groups that contain heteroatoms in the ring, such as, for example -(CH2CH2NR")v- wherein R" can be a branched or unbranched divalent alkyl chain of 1-16 carbons with or without heteroatoms substituted into the R" chain.

-Aryl-, above, is a substituted or unsubstituted divalent aromatic group, such aromatic groups include, for example the phenylenes (-C6H4-), the fused divalent aromatic group, such as, for example, the naphthylenes (-C10H6-), the anthacenylenes (-C14H8-) and the like, as well as the heteroaromatic groups, such as, for example, the nitrogen heterocycles: pyridines, quinolines, pyrroles, indoles, pyrazoles, the triazines, and other nitrogen-containing aromatic heterocycles well known in the arts, as well as the oxygen heterocycles: furans, oxazoles and other oxygen-containing aromatic heterocycles, as well the sulfur containing aromatic heterocycles, such as, for example, thiophenes.

Turning to the leaving groups, LG, on at least one of X or Y, LG may be H or D as long as the other of X or Y comprises an acid labile group. Leaving groups are taken to be those groups that may be removed or are removable by acidolysis, and may include, for example and without limitation, tertiary alkyl leaving groups, which have the general structure —CR$_5$R$_6$R7, wherein R$_5$, R6, and R7 may be the same or different and represent linear or branched alkyl, heteroalkyl or alkyl aryl groups. Without limitation, exemplary groups may be a tert-butyl group, a tert-pentyl group, a 2,3-dimethylbutan-2-yl group, a 2,3,3-trimethylbutan-2-yl group, a 2,3-dimethylpentan-3-yl group, a 2-methylbicyclo[2.2.1]heptan-2-yl group, a bicyclo[2.2.1]heptan-2-yl group, a 1-methylcyclopentyl group, a 1-ethylcyclopentyl group, a 1-methylcyclohexyl group, a 1-ethylcyclohexyl group, a 2-methyladamantyl group or a 2-ethyladamantyl group. Further, exemplary tertiary carbon containing leaving groups may include ring structures having oxygen atoms such as a mevalonic lactone-yl group.

Leaving groups may also include, without limitation, ketals. Exemplary ketals include, without limitation, methoxycyclopropanyl, ethoxycyclopropanyl, butoxycyclohexanyl, methoxycyclobutanyl, ethoxycyclobutanyl, methoxycyclopentanyl, ethoxycyclopentanyl, methoxycyclohexanyl, ethoxycyclohexanyl, propoxycyclohexanyl, methoxycycloheptanyl, methoxycyclooctanyl or methoxyadamantyl.

Leaving groups may also include acetals. Acetals may be derived from known reactions with vinyl ethers to produce esterified leaving groups, such as alkoxyalkyl esters. Vinyl ethers that may be used for this purpose include methyl vinyl ether, ethyl vinyl ether, butyl vinyl ether, cyclohexyl vinyl ether, 2-phenoxyethyl vinyl ether, phenyl vinyl ether, and p-methoxyphenyl vinyl ether.

In addition, LG may be, for example, substituted methyl groups, 1-substituted ethyl groups, 1-substituted alkyl groups, silyl groups, germyl groups, alkyl carbonyl groups, acyl groups and cyclic acid-dissociable groups. The substituted methyl groups include, for example, the methoxymethyl group, methylthiomethyl group, ethoxy methyl group, ethylthiomethyl group, methoxyethoxy methyl group, benzyloxymethyl group, benzylthiomethyl group, phenacyl group, bromophenacyl group, methoxyphenacyl group, methylthiophenacyl group, a-methylphenacyl group, cyclopropylmethyl group, benzyl group, diphenyl methyl group, triphenylmethyl group, bromobenzyl group, nitrobenzyl group, methoxybenzyl group, methylthiobenzyl group, ethoxy benzyl group, ethylthiobenzyl group, piperonyl group, methoxycarbonylmethyl group, ethoxy carbonylmethyl group, N-propoxy carbonylmethyl group, isopropoxy carbonylmethyl group, N-butoxycarbonylmethyl group and t-butoxycarbonylmethyl group. The 1-substituted ethyl groups include, for example. 1-methoxyethyl group, 1-methylthioethyl group, 1,1-dimethoxyethyl group, 1-ethoxy ethyl group, 1-ethylthioethyl group, 1,1-diethoxy ethyl group, 1-phenoxyethyl group, 1-phenylthioethyl group, 1,1-diphenoxyethyl group, 1-benzyloxyethyl group, 1-benzylthioethyl group, 1-cyclopropylethyl group, 1-phenylethyl group, 1,1-diphenyl ethyl group, 1-methoxycarbonylethyl group, 1-ethoxy carbonylethyl group, 1-N-propoxy carbonylethyl group, 1-isopropoxy carbonylethyl group, 1-N-butoxycarbonylethyl group and the 1-t-butoxycarbonylethyl group. The 1-substituted alkyl group include the isopropyl group, sec-butyl group, t-butyl group, 1,1-dimethylpropyl group, 1-methylbutyl group and 1,1-dimethylbutyl group.

The silyl acid leaving groups include, for example, the trimethyl silyl group, ethyldimethylsilyl group, methyldiethylsilyl group, triethylsilyl group, isopropyldimethylsilyl group, methyldiisopropylsilyl group, triisopropylsilyl group, t-butyldimethylsilyl group, methyldi-t-butylsilyl group, tri-t-butylsilyl group, phenyldimethylsilyl group, methyldiphenyl silyl group and triphenylsilyl group. The germyl groups include, for example, the trimethyl germyl group, ethyldimethylgermyl group, methyldiethylgermyl group, triethylgermyl group, isopropyldimethylgermyl group, methyldiisopropylgermyl group, triisopropylgermyl group, t-butyldimethylgermyl group, methyldi-t-butylgermyl group, tri-t-butylgermyl group, phenyldimethylgermyl group, methyldiphenyl germyl group and triphenylgermyl group.

The alkoxycarbonyl leaving groups include the methoxycarbonyl group, ethoxy carbonyl group, isopropoxy carbonyl group and t-butoxycarbonyl group. The acyl acid labile groups include, for example, the acetyl group, propionyl group, butyryl group, heptanoyl group, hexanoyl group, valeryl group, pivaloyl group, isovaleryl group, lauroyl group, myristoyl group, palmitoyl group, stearoyl group, oxaryl group, malonyl group, succinyl group, glutaryl group, adipoyl group, piperoyl group, suberoyl group, azelaoyl group, sebacoyl group, acrylyl group, propioloyl group, methacryloyl group, crotonoyl group, oleoyl group, maleoyl group, fumaroyl group, mesaconoyl group, camphoroyl group, benzoyl group, phthaloyl group, isophthaloyl group, terephthaloyl group, naphthoyl group, toluoyl group, hydroatropoyl group, atropoyl group, cinnamoyl group, furoyl group, thenoyl group, nicotinoyl group, isonicotinoyl group, p-toluene sulfonyl group and the mesyl group.

Leaving groups may also include ring or alicyclic structures that may be removed by acidolysis such as, for example, a cyclopropyl group, cyclopentyl group, cyclohexyl group, cyclohexanyl group, 4-methoxycyclohexyl group, tetrahydropyranyl group, tetrahydrofuranyl group, tetrahydrothiopyranyl group, tetrahydrothiofuranyl group, 3-bromo tetrahydropyranyl group, 4-methoxy tetrahydropyranyl group, 4-methoxy tetrahydrothiopyranyl group and 3-tetrahydrothiophene-1,1-dioxy group.

Without intending to be bound by theory, it is believed that the $CBr_4$ functions in the coupling reactions of FIGS. 1 and 2 as a bromonium, halonium or pseudo halonium source in the reaction to substitute for one of the hydrogen atoms on the central malonate carbon atom. Suitable replacements for $CBr_4$ may be $CCl_4$, $I_2$, $Br_2$, an aryl cyanate such as phenyl cyanate, cyanogen, or N-bromosuccinimide.

Photoresist materials comprise an ester material such as (I)-(VIII), which takes the place of at least a portion of the resin in a conventional photoresist, and a photoacid generator. The discussion below describes useful photoacid generators for this purpose.

The above described compositions of matter may further comprise, in admixture, photoacid generators. Without limitation, these may include onium salt compounds, such as sulfonium salts, phosphonium salts or iodonium salts, sulfone imide compounds, halogen-containing compounds, sulfone compounds, ester sulfonate compounds, quinone diazide compounds, diazomethane compounds, dicarboximidyl sulfonic acid esters, ylideneaminooxy sulfonic acid esters, sulfanyldiazomethanes, or a mixture thereof.

Specific examples of photoacid generators include include diphenyl(4-phenylthiophenyl)sulphonium hexafluoroantimonate, 4,4'-bis[diphenylsulfoniolphenylsulphide bis hexafluoroantimonate and combinations there of, triphenylsulfonium nonafluorobutanesulfonate, triphenylsulfonium trifluoromethanesulfonate, triphenylsulfonium pyrenesulfonate, triphenylsulfonium dodecylbenzenesulfonate, triphenylsulfonium p-toluene sulfonate, triphenylsulfonium benzenesulfonate, triphenylsulfonium 10-camphor-sulfonate, triphenylsulfonium (perfluoro)octanesulfonate, triphenylsulfonium 2-trifluoromethyl benzenesulfonate, triphenylsulfonium hexafluoroantimonate, triarylsulfonium hexafluoroantimonates, the triarylsulfonium hexafluorophosphates, the triarylsulfonium tetrafluoroborates as well as other tetrafluoroborates, triphenylsulfonium napthalenesulfonate, tri(4-hydroxyphenyl)sulfonium nonafluorobutanesulfonate, tri(4-hydroxyphenyl)sulfoniumtrifluoromethanesulfonate, tri(4-hydroxyphenyl)sulfonium pyrenesulfonate, tri(4-hydroxyphenyl) sulfoniumdodecylbenzenesulfonate, tri(4-hydroxyphenyl)sulfonium p-toluene sulfonate, tri(4-hydroxyphenyl)sulfonium benzenesulfonate, tri(4-hydroxyphenyl)sulfonium10-camphor-sulfonate, tri(4-hydroxyphenyl)sulfonium (perfluoro)octanesulfonate, tri(4-hydroxyphenyl)sulfonium 2-trifluoromethylbenzenesulfonate, tri(4-hydroxyphenyl) sulfonium hexafluoroantimonate, tri(4-hydroxyphenyl)sulfonium napthalenesulfonate, diphenyliodonium nonafluorobutanesulfonate, diphenyliodonium trifluoromethanesulfonate, diphenyliodonium pyrenesulfonate, diphenyliodonium dodecylbenzenesulfonate, diphenyliodonium p-toluene sulfonate, diphenyliodonium benzenesulfonate, diphenyliodonium 10-camphor-sulfonate, diphenyliodonium (perfluoro)octanesulfonate, diphenyliodonium 2-trifluoromethylbenzenesulfonate, bis(4-t-butylphenyl)iodonium nonafluorobutanesulfonate, bis(4-t-butylphenyl)iodonium trifluoromethanesulfonate, bis(4-t-butylphenyl) iodonium pyrenesulfonate, bis(4-t-butylphenyl)iodonium dodecylbenzenesulfonate, bis(4-t-butylphenyl)iodonium p-toluene sulfonate, bis(4-t-butylphenyl)iodonium benzenesulfonate, bis(4-t-butylphenyl)iodonium 10-camphor-sulfonate, bis(4-t-butylphenyl)iodonium (perfluoro)octanesulfonate, bis(4-t-butylphenyl)iodonium 2-trifluoromethylbenzenesulfonate, 4-hydroxy-1-naphthyl tetrahydrothiophenium trifluoromethanesulfonate and 4,7-dihydroxy-1-naphthyl tetrahydrothiophenium trifluoromethanesulfonate.

Specific examples of a sulfone imide compound include N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hepto-5-ene-2,3-dicarboxyimide,N-(trifluoromethylsulfonyloxy)-7-oxabicyclo [2.2.1]hepto-5-ene-2,3-dicarboxyimide, N-(trifluoromethylsulfonyloxy) bicyclo[2.2.1]heptane-5,6-oxy-2,3-dicarboxyimide, N-(trifluoromethylsulfonyloxy)naphthylimide, N-(10-camphor-sulfonyloxy)succinimide, N-(10-camphor-sulfonyloxy)phthalimide, N-(10-camphor-sulfonyloxy)diphenyl maleimide, N-(10-camphor-sulfonyloxy)bicyclo[ hepto-5-ene-2,3-dicarboxyimide, N-(10-camphor-sulfonyloxy)-7-oxabicyclo[2.2.1]hepto-5-ene-2,3-dicarboxyimide, N-(10-camphor-sulfonyloxy)bicyclo[2.2.1]heptane-5,6-oxy-2,3-dicarboxyimide, N-(10-camphor-sulfonyloxy) naphthylimide, N-(p-toluene sulfonyloxy) succinimide, N-(p-toluene sulfonyloxy)phthalimide, N-(p-toluene sulfonyloxy)diphenyl maleimide, N-(p-toluene sulfonyloxy)bicyclo[2.2.1]hepto-5-ene-2,3-dicarboxyimide, N-(p-toluene sulfonyloxy)-7-oxabicyclo[2.2.1]hepto-5-ene-2,3-dicarboxyimide, N-(p-toluene sulfonyloxy) bicyclo[2.2.1]heptane-5,6-oxy-2,3-dicarboxyimide, N-(p-toluene sulfonyloxy)naphthylimide, N-(2-trifluoromethylbenzenesulfonyloxy)succinimide, N-(2-trifluoromethylbenzenesulfonyloxy)phthalimide, N-(2-trifluoromethylbenzenesulfonyloxy)diphenyl maleimide, N-(2-trifluoromethylbenzenesulfonyloxy)bicyclo[2.2.1] hepto-5-ene-2,3-dicarboxyimide, N-(2-trifluoromethylbenzenesulfonyloxy)-7-oxabicyclo[2.2.1]hepto-5-ene-2,3-dicarboxyimide, N-(2-trifluoromethylbenzenesulfonyloxy) bicyclo[2.2.1]heptane-5,6-oxy-2,3-dicarboxyimide, N-(2-trifluoromethylbenzenesulfonyloxy) naphthylimide, N-(4-fluorobenzenesulfonyloxy)succinimide, N-(4-fluorobenzenesulfonyloxy)phthalimide, N-(4-fluorobenzenesulfonyloxy)diphenyl maleimide, N-(4-fluorobenzenesulfonyloxy)bicyclo[2.2.1]hepto-5-ene-2,3-dicarboxyimide, N-(4-fluorobenzenesulfonyloxy)-7-oxabicyclo[2.2.1]hepto-5-ene-2,3-dicarboxyimide, N-(4-fluorobenzenesulfonyloxy) bicyclo[2.2.1]heptane-5,6-oxy-2,3-dicarboxyimide, N-(4-fluorobenzenesulfonyloxy) naphthylimide, N-(nonafluorobutylsulfonyloxy) succinimide, N-(nonafluorobutylsulfonyloxy)phthalimide, N-(nonafluorobutylsulfonyloxy)diphenyl maleimide, N-(nonafluorobutylsulfonyloxy)bicyclo[2.2.1]hepto-5-ene-2,3-dicarboxyimide, N-(nonafluorobutylsulfonyloxy)-7-oxabicyclo[2.2.1]hepto-5-ene-2,3-dicarboxyimide, N-(nonafluorobutylsulfonyloxy) bicyclo[2.2.1]heptane-5,6-oxy-2,3-dicarboxyimide and N-(nonafluorobutylsulfonyloxy) naphthylimide.

Examples of halogen-containing compounds include, for example, haloalkyl group-containing hydrocarbon compounds and haloalkyl group-containing heterocyclic compounds. Specific examples of halogen-containing compounds include (poly)trichloromethyl-s-triadine derivatives such as phenyl-bis(trichloromethyl)-s-triadine, 4-methoxyphenyl-bis(trichloromethyl)-s-triadine and 1-naphthyl-bis(trichloromethyl)-s-triadine, and 1,1-bis(4-chlorophenyl)-2,2,2-trichloroethane.

Examples of sulfone compounds include, for example, P-ketosulfone and P-sulfonylsulfone, and the a-diazo compounds thereof. Specific examples of the sulfone compounds include phenacyl phenylsulfone, mesitylphenacyl sulfone, bis(phenylsulfonyl)methane, 1,1-bis(phenylsulfonyl) cyclobutane, 1,1-bis(phenylsulfonyl) cyclopentane, 1,1-bis (phenylsulfonyl) cyclo hexane, and 4-trisphenacyl sulfone.

Examples of sulfonate ester compounds include alkylsulfonate esters, haloalkyl sulfonate esters, aryl sulfonate esters sand imino sulfonates. Specific examples of sulfonate ester compounds include benzoin tosylate, pyrogallol tristrifluoromethanesulfonate, pyrogallol trisnonafluorobutanesulfonate, pyrogallol (perfluoro)methanesulfonate triester, nitrobenzyl-9,10-diethoxy anthracene-2-sulfonate, a-methylol benzoin tosylate, α-methylol benzoin (perfluoro)octanesulfonate, α-methylol benzoin trifluoromethanesulfonate and α-methylol benzoin dodecylsulfonate.

Examples of quinine diazide compounds include compounds containing a 1,2-quinone diazide sulfonyl group such as the 1,2-benzoquinone diazide-4-sulfonyl group, 1,2-naphthoquinone diazide-4-sulfonyl group, 1,2-naphtho quinine diazide-5-sulfonyl group and 1,2-naphthoquinone diazide-6-sulfonyl group. Specific examples of quinone diazide compounds include 1,2-quinone diazidesulfonate esters of (poly) hydroxyphenylaryl ketones such as 2,3,4-trihydroxybenzophenone, 2,4,6-trihydroxybenzophenone, 2,3,4,4'-tetrahydroxybenzophenone, 2,2',3,4-tetrahydroxybenzophenone, 3'-methoxy-2,3,4,4'-tetrahydroxybenzophenone, 2,2',4,4'-tetrahydroxybenzophenone, 2,2'3,4,4'-pentahydroxybenzophenone, 2,2'3,4,6'-pentahydroxybenzophenone, 2,3,3'4,4',5'-hexahydroxybenzophenone, 2,3'4,4',5',6-hexahydroxybenzophenone; 1,2-quinone diazide sulfonate esters of bis[(poly) hydroxyphenyl]alkanes such as bis(4-hydroxyphenyl) methane, bis(2,4-dihydroxyphenyl) methane, bis(2,3,4-trihydroxyphenyl) methane, 2,2-bis(4-hydroxyphenyl) propane, 2,2-bis(2,4-dihydroxyphenyl) propane and 2,2-bis(2,3,4-trihydroxyphenyl) propane; 1,2-quinone diazide sulfonate esters of (poly) hydroxytriphenylalkanes such as 4,4'-dihydroxytriphenylmethane, 4,4',4"-trihydroxytriphenylmethane, 2,2',5,5'-tetramethyl-2"',4,4'-trihydroxytriphenylmethane, 3,3',5,5'-tetramethyl-2"',4,4'-trihydroxytriphenylmethane, 4,4',5,5'-tetramethyl-2,2',2"'-trihydroxytriphenylmethane, 2,2',5,5'-tetramethyl-4,4',4"'-trihydroxytriphenylmethane, 1,1,1-tris (4-hydroxyphenyl) ethane, 1,1-bis(4-hydroxyphenyl)-1-phenylethane, 1,1-bis (4-hydroxyphenyl)-1-[4-{1-(4-hydroxyphenyl)-1-methylethyl}phenyl]ethane, 1,1,3-tris (2,5-dimethyl-4-hydroxyphenyl) propane, 1,1,3-tris (2,5-dimethyl-4-hydroxyphenyl) butane and 1,3,3-tris (2,5-dimethyl-4-hydroxyphenyl) butane; and 1,2-quinone diazide sulfonate esters of (poly) hydroxyphenylflavans such as 2,4,4-trimethyl-2',4',7-trihydroxy-2-phenylflavan and 2,4,4-trimethyl-2',4',5',6',7-pentahydroxy-2-phenylflavan.

Specific examples of diazomethane compounds include bis(trifluoromethylsulfonyl)diazomethane, bis(cyclohexylsulfonyl)diazomethane, bis(phenylsulfonyl) diazomethane, bis(p-toluene sulfonyl) diazomethane, methylsulfonyl-p-toluene sulfonyldiazomethane, 1-cyclohexylsulfonyl-1-(1,1-dimethylethylsulfonyl)diazomethane and bis(1,1-dimethylethylsulfonyl)diazomethane.

Negative working materials may also comprise a crosslinker. Crosslinkers, suitable for the current disclosure, comprise compounds able to cross-link with the above disclosed ester, after it is deprotected, but, in any case, if either X or Y comprise functional groups that can be reacted with the crosslinker. Among these reactive functional groups are alcohols, phenols, protic amides, carboxylic acids and the like. Before the deprotection reaction occurs, at least a portion of the reactive functional groups are protected by an acid labile group described above. Once the deprotection reaction occurs, the crosslinker may react with the deprotected functional group. Not to be held to theory, it is believed that the photogenerated acid not only reacts with the acid-labile group of the above disclosed ester but aids in the reaction of the crosslinker with itself and the ester. Examples of crosslinkers include compounds comprising at least one type of substituted group that possess a cross-linking reactivity with the phenol or similar group of the on the deprotected ester. Specific examples of this crosslinking group include, without limitation, the glycidyl ether group, the oxetane group, glycidyl ester group, glycidyl amino group, methoxymethyl group, ethoxy methyl group, benzyloxymethyl group, dimethylamino methyl group, diethylamino methyl group, dimethylol amino methyl group, diethylol amino methyl group, morpholino methyl group, acetoxymethyl group, benzyloxy methyl group, formyl group, acetyl group, vinyl group and isopropenyl group.

Non limiting examples of compounds having the aforementioned cross-linking substituted group include, bisphenol A-based epoxy compounds, bisphenol F-based epoxy compounds, bisphenol S-based epoxy compounds, novolac resin-based epoxy compound, resol resin-based epoxy compounds, poly (hydroxystyrene)-based epoxy compounds, (3-ethyloxetan-3-yl)methanol, 1,3-bis(((3-ethyloxetan-3-yl)methoxy)methyl)benzene, 3,3'-oxybis(methylene)bis(3-ethyloxetane), and phenol novolak oxetane, sold by Toagosei America Inc. of West Jefferson, Ohio, as OXT-101, OXT-121, OXT-221 and PNOX1009, respectively, methylol group-containing melamine compounds, methylol group-containing benzoguanamine compounds, methylol group-containing urea compounds, methylol group-containing phenol compounds, alkoxyalkyl group-containing melamine compounds, alkoxyalkyl group-containing benzoguanamine compounds, alkoxyalkyl group-containing urea compounds, alkoxyalkyl group-containing phenol compounds, carboxymethyl group-containing melamine resins, carboxy methyl group-containing benzoguanamine resins, carboxymethyl group-containing urea resins, carboxymethyl group-containing phenol resins, carboxymethyl group-containing melamine compounds, carboxymethyl group-containing benzoguanamine compounds, carboxymethyl group-containing urea compounds, and carboxymethyl group-containing phenol compounds, methylol group-containing phenol compounds, methoxymethyl group-containing melamine compounds, methoxymethyl group-containing phenol compounds, methoxymethyl group-containing glycol-uril compounds, methoxymethyl group-containing urea compounds and acetoxymethyl group-containing phenol compounds. The methoxymethyl group-containing melamine compounds are commercially available as, for example, CYMEL300, CYMEL301, CYMEL303, CYMEL305 (manufactured by Mitsui Cyanamid), the methoxymethyl group-containing glycol-uril compounds are commercially available as, for example, CYMEL117 4 (manufactured by Mitsui Cyanamid), and the methoxymethyl group-containing urea compounds are commercially available as, for example, MX290 (manufactured by Sanwa Chemicals).

A photosensitive composition comprising the above compositions of matter may further comprise a solvent to enable spin coating on a semiconductor, other device in process, or other work piece. Suitable solvents include ethers, esters, etheresters, ketones and ketoneesters and, more specifically, ethylene glycol monoalkyl ethers, diethylene glycol dialkyl ethers, propylene glycol monoalkyl ethers, propylene glycol dialkyl ethers, alkyl phenyl ethers such as anisole, acetate esters, hydroxyacetate esters, lactate esters, such as ethyl lactate, methyl lactate, propyl lactate, butyl lactate, ethylene glycol monoalkylether acetates, propylene glycol monoalkylether acetates, alkoxyacetate esters, (non-)cyclic ketones, acetoacetate esters, pyruvate esters and propionate esters. Specific examples of these solvents include ethylene glycol monomethyl ether, ethylene glycol monoethyl ether, ethylene glycol monopropyl ether, ethylene glycol monobutyl ether, diethylene glycol dimethyl ether, diethylene glycol diethyl ether, diethylene glycol dipropyl ether, diethylene glycol dibutyl ether, methylcellosolve acetate, ethyl cellosolve acetate, propylene glycol monomethyletheracetate, propylene glycol monoethyletheracetate, propylene glycol monopropyletheracetate, isopropenyl acetate, isopropenyl propionate, methylethyl ketone, cyclohexanone, 2-heptanone, 3-heptanone, 4-heptanone, 2-hydroxypropionate ethyl, 2-hydroxy-2-methylpropionate ethyl, ethoxy acetate ethyl, hydroxyacetate ethyl, 2-hydroxy-3-methyl methylbutyrate, 3-methoxybutylacetate, 3-methyl-3-methoxybutylacetate, 3-methyl-3-methoxybutyl propionate, 3-methyl-3-methoxybutyl butylate, ethyl acetate, propyl acetate, butyl acetate, methyl acetoacetate, ethyl acetoacetate, methyl 3-methoxypropionate, ethyl 3-methoxy propionate, 3-ethoxy propionate methyl and 3-ethoxy propionate ethyl. The aforementioned solvents may be used independently or as a mixture of two or more types. Furthermore, at least one type of high boiling point solvent such as benzylethyl ether, dihexyl ether, diethylene glycol monomethyl ether, diethylene glycol monoethyl ether, acetonylacetone, isoholon, caproic acid, capric acid, 1-octanol, 1-nonanol, benzyl alcohol, benzyl acetate, ethyl benzoate, diethyl oxalate, diethyl maleate, y-butyrolactone, ethylene carbonate, propylene carbonate and phenylcellosolve acetate may be added to the aforementioned solvent.

Various additives may be added to the photoresist formulations to provide certain desirable characteristics of the photosensitive composition such as, for example, acid diffusion control agents to retard acid from migrating into unexposed areas of the coating, surfactants and leveling agents to improve coating of substrates, adhesion promoters to improve adhesion of the coating to the substrate and sensitizers to improve the photosensitivity of the photosensitive composition coating during photoexposure, and antifoaming agents and air release agents, as well as other materials well known in the coatings industry.

Some photoresists may additionally encompass one or more optional components or additives in addition to the aforementioned composition of matter, photoacid generators and solvents. Such components include base quenchers. Suitable base quenchers include, but are not limited to, tetramethylammonium hydroxide, triethanolamine, triisopropylamine, N-methylpyrrolidone, 1,8-diazabicyclo[5.4.0]undec-7-ene (DBU), 1,5-diazabicyclo[4.3.0]non-5-ene (DBN), 7-Methyl-1,5,7-triazabicyclo(4.4.0)dec-5-ene, quinuclidine, carboxylate salts such as tetramethylammonium acetate, tetramethylammonium lactate, tetramethylammonium propanoate, and the like.

The photosensitive compositions can be coated onto substrate such as a silicon wafer or a wafer coated with silicon dioxide, aluminium, aluminum oxide, copper, nickel, any of a number of semiconductor materials or nitrides or other substrates well known the semiconductor industry, or a substrate having thereon an organic film, such as, for example, a bottom layer anti-reflective film or the like. The photoresist compositions are applied by such processes as spin coating, curtain coating, slot coating, dip coating, roller coating, blade coating, ultrasonic coating, vapor coating and the like. After coating, the solvent is removed, if applicable, to a level wherein the coating can be properly exposed, abd baked and developed, if applicable. In some cases a residual of 5% solvent may remain in the coating while in other cases less than 1% is required. Drying can be accomplished by hot plate heating, convection heating, infrared heating and the like. The coating is then imagewise exposed through a mark containing a desired pattern or flood exposed.

Radiation suitable for the described photosensitive compositions include, for example, ultraviolet rays (UV), such as the bright line spectrum of a mercury lamp (254 nm), a KrF excimer laser (248 nm), and an ArF excimer laser (193 nm), an $F_2$ excimer laser (157 nm), extreme ultraviolet (EUV) such as 13.5 nm from plasma discharge and synchrotron light sources, beyond extreme ultraviolet (BEUV) such as 6.7 nm exposure, X-ray such as synchrotron radiation. Ion beam lithography and charged particle rays such as electron beams may also be used.

Following exposure, the exposed coated substrate may optionally be post exposure baked to enhance the reaction of the generated photoacid, such as, for example, heating from about 30 to about 350° C. for about 10 to about 600 seconds. This may be accomplished by hot plate heating, convection heating, infrared heating and the like. The heating may also be performed by a laser heating processes such as, for example, a $CO_2$ laser pulse heating for about 2 to about 5 milliseconds. Both heating processes may be combined in tandem.

A flood exposure process may be applied after the pattern exposure to aid in further cure.

Results have indicated that flood exposure reduces or eliminates pattern collapse after development of the negative-tone resists as well as reduction in line edge roughness. For example, a 532 nm continuous wave laser exposes the previously exposed resist for 1-2 sec followed by wet development. The flood process may or may not be followed by a heating step.

The exposed film is then developed using a suitable a developer. Such developers include organic solvents as well as aqueous solutions such as aqueous alkali solutions known in the art. When an organic solvent is used to remove the unexposed areas generally the solvent is less aggressive than the solvent that was used in preparing the photoresist composition. Examples of aqueous alkali development solution include, for example, at least one type of alkaline compound such alkali metal hydroxides, ammonia water, alkylamines, alkanolamines, heterocyclicamines, tetraalkyl ammonium hydroxides such as tetramethyl ammonium hydroxide, cholines, and 1,8-diazabicyclo[5.4.0]-7-undecan, 1,5-diazabicyclo[4.3.0]-5-nonene at a concentration of about 1 to about 10% by weight, such as, for example, about 2 to about 5% by weight. Water-soluble organic solvents such as methanol and ethanol and surfactants may also be added in suitable amounts to the alkaline aqueous solution, depending on the desired development characteristics and process parameters.

After development a final baking step may be included to further enhance the curing of the now exposed and developed pattern. The heating process may be, for example, from about 30 to about 350° C. for about 10 to about 120 seconds and may be accomplished by hot plate heating, convection heating, infrared heating and the like.

EXAMPLES

Synthesis Example 1

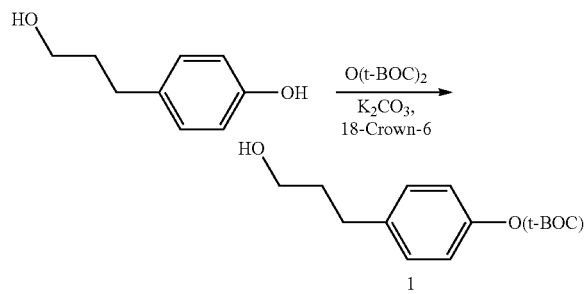

1

To a 3 L round bottom flask was added 3-(4-hydroxyphenyl)-1-propanol (102.1 g, 670.9 mmol), dichloromethane (760 mL) and di-tert-butyldicarbonate (146.4 g, 670.9 mmol). The mixture was stirred under nitrogen and cooled to 0° C. in an ice bath. Potassium carbonate (250.3 g, 1811.3 mmol) and 18-crown-6 (8.9 g, 33.5 mmol) were added. The resulting mixture was stirred and warmed to room temperature overnight. The crude reaction mixture was evaporated to remove most of the solvent and the residue was purified via flash column chromatography on silica gel with ethyl acetate:Hexane (40%/60%) as eluant. The third fraction was combined together and the solvent removed to give 135.6 g (yield: 80%) of 1 as a yellow oil. The product was characterized by $^1$H NMR.

Synthesis Example 2

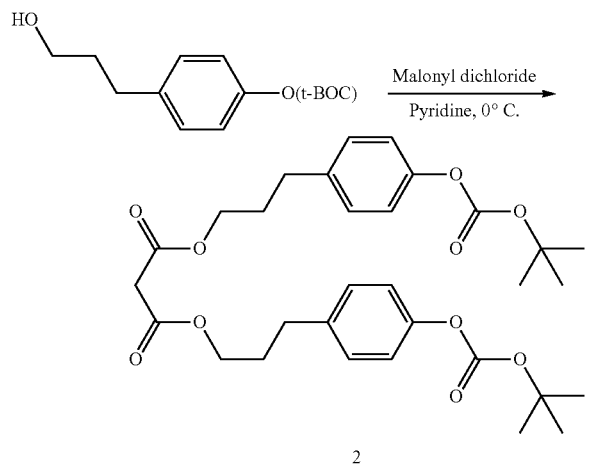

2

Dichloromethane (2 L) was added to 1 (135.6 g, 537.7 mmol) in a 3 L round bottom flask. To this was added, while stirring, pyridine (56.6 g, 715.1 mmol) and the solution was cooled to 0° C. in an ice bath under nitrogen. Malonyl dichloride (34.8 mL, 357.6 mmol) was added dropwise using an addition funnel. The initially clear solution became dark red upon complete addition of the malonyl dichloride. The mixture was stirred and warmed up to room temperature overnight, by which time it had become dark blue/green in color. The mixture was filtered through a silica gel plug which was rinsed with ethyl acetate. The filtrate was evaporated and the residue was purified via flash column chromatography on silica gel using 25% ethyl acetate/n-hexane as eluant. The fractions were collected and solvent was removed to give 2 as yellow oil (93.1 g, 61% yield). The product was characterized by $^1$H NMR.

Synthesis Example 3

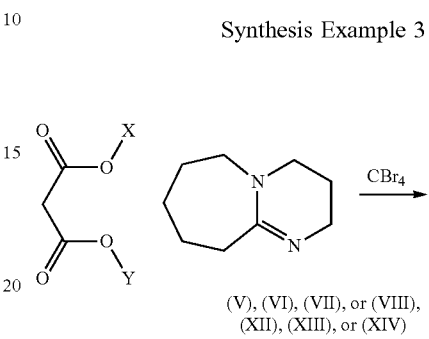

(V), (VI), (VII), or (VIII), (XII), (XIII), or (XIV)

m = 2
n = 3

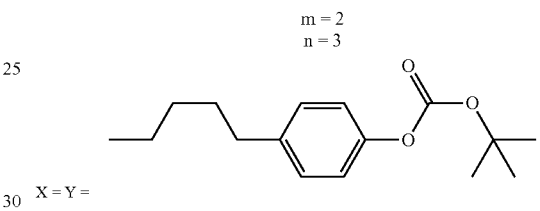

X = Y =

Tetrabromomethane (4.05 g, 12.2 mmol) and 2 (6.3 g, 11.0 mmol) were added to a 500 mL round bottom flask. Toluene (240 mL) was added and the mixture was stirred under nitrogen for 1 hour. 1,8-Diazabicyclo[5.4.0]undec-7-ene (DBU, 7.3 g, 48.2 mmol) was added dropwise. The reaction mixture was stirred under nitrogen for 18 hours and then filtered. The resulting mixture was purified via a silica gel column using toluene, followed by ethyl acetate and then a gradient of 20% to 50% isopropanol/ethyl acetate. The fifth fraction was collected and solvent was removed to give the final product as a light yellow solid (3.4 g). The product was characterized by $^1$H NMR and elemental analysis and $^{13}$C NMR analysis which showed that the most likely product was (V), wherein m=2 and n=3.

Synthesis Example 4

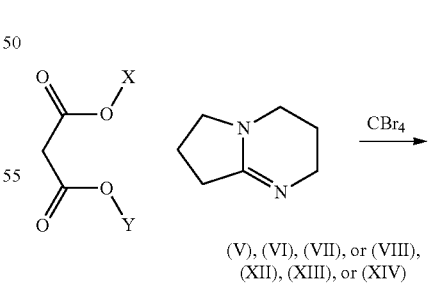

(V), (VI), (VII), or (VIII), (XII), (XIII), or (XIV)

m = 2
n = 1

X = Y = 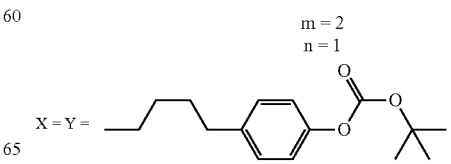

Similar to Synthesis Example 3 except that 1,5-Diazabicyclo(4.3.0)non-5-ene (DBN, 5.95 g, 48.2 mmol) was used. The product was characterized by $^1$H NMR.

Formulation Example 1

In a hypothetical formulation, 1 g of the product of Synthesis Example 3 is combined with 0.2 g of triphenylsulfonium tosylate and 200 g of propylene glycol methyl ether acetate. The mixture is placed on a roller mill, rolled until dissolved, and filtered through a 20 nm PTFE membrane filter, available from Pall Corporation, of Port Washington N.Y.

Structure Determination Example

The product resulting from Synthesis Example 4 was used in the following structural determination. Crystals were obtained by solvent vapor diffusion. A dried sample (3 mg) was dissolved in toluene (5 ml) in a small vial, which was then placed inside a larger vessel filled with hexane (20 ml). The vessel was sealed and kept at room temperature. Yellow crystals appeared at the bottom of vial after 5 days.

A single crystal, chosen from among several, was found to be the most suitable for X-ray crystallographic analysis and was used for structural determination. X-ray intensity data were measured at 100(2) K (Oxford Cryostream 700) on a Bruker Kappa APEX Duo diffractometer system equipped with a sealed Mo-target X-ray tube (X=0.71073 Å) and a high brightness IµS copper source (X=1.54178 Å). The crystals were mounted on a goniometer head with paratone oil. The detector was placed at a distance of 5.000 cm from the crystal. For each experiment, data collection strategy was determined by APEX software package and all frames were collected with a scan width of 0.5° in w and 4 with an exposure time of 10 or 20 s/frame. The frames were integrated as a 2-component twin with the Bruker SAINT Software package using a narrow-frame integration algorithm to a maximum 2θ angle of 56.54° (0.75 Å resolution) for Mo data and 134° (0.84 Å resolution) for Cu data. The final cell constants were based upon the refinement of the XYZ-centroids of several thousand reflections above 20 σ(I). Analysis of the data showed negligible decay during data collection. Data were corrected for absorption effects using the empirical method (TWINABS). The structure was solved and refined by full-matrix least squares procedures on |F$^2$| using the Bruker SHELXTL (version 2014-6) software package. All hydrogen atoms were included in idealized positions for structure factor calculations except for those forming hydrogen bonds. Anisotropic displacement parameters were assigned to all non-hydrogen atoms. Crystal data are shown in Table 1. A rendering of the structure is given in FIG. 4. The basic structure is given below:

The structure appears to have a zwitterionic character having two positively charged quaternized nitrogen atoms (as shown), a negatively charged carbanion (as shown) and a hydroxide counterion, which

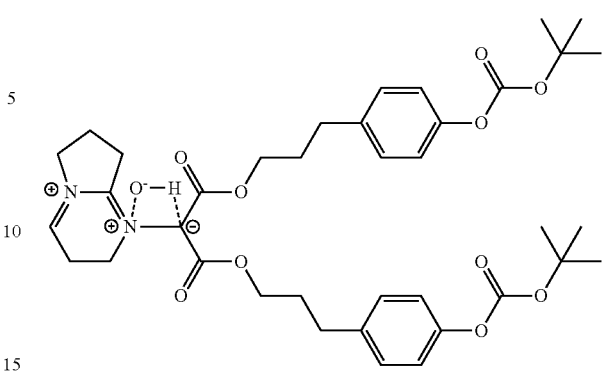

appears to exhibit hydrogen bonding with the basic structure. It should be understood that the charges shown in the structure are formal charges. They do not represent any form of measurement and are not intended to bind us by theory.

TABLE 1

| Crystal Data for [$(C_{38}H_{49}N_2O_{10})^+(OH)^-$] | |
| --- | --- |
| Identification code | [$(C_{38}H_{49}N_2O_{10})^+(OH)^-$] |
| Empirical formula | $C_{38}H_{50}N_2O_{11}$ |
| Formula weight | 710.8 Daltons |
| Temperature | 100(2) K |
| Wavelength | 0.71073 Å |
| Crystal system | Monoclinic |
| Space group | C 2/c |
| Unit cell dimensions | a = 46.903(7) Å, α = 90° |
| | b = 5.5064(7) Å, β = 104.321(7)° |
| | c = 14.628(2) Å, γ = 90° |
| Volume | 3660.6(9) Å$^3$ |
| Z | 4 molecules per cell |
| Density (calculated) | 1.290 mg/m$^3$ |
| Absorption coefficient | 0.095 mm$^{-1}$ |
| F(000) | 1520 |
| Crystal size | 0.40 × 0.22 × 0.08 mm$^3$ |
| Theta range for data collection | 2.689° to 28.486°. |
| Index ranges | −7 <= h <= 62, −7 <= k <= 7, |
| | −19 <= l <= 18 |
| Reflections collected | 8662 |
| Independent reflections | 8662 [R(int) = 0.0871] |
| Completeness to | θ = 25.242° 99.9% |
| Max. and min. transmission | 1 and 0.4921 |
| Data/restraints/parameters | 8662/250/324 |
| Goodness-of-fit on F2 | 1.02 |
| Final R indices [I > 2sigma(I)] | R$_1$ = 0.0744, wR$_2$ = 0.1496 |
| R indices (all data) | R$_1$ = 0.1408, wR$_2$ = 0.1792 |
| Largest diff. peak and hole | 0.384 and −0.276 e · Å$^{-3}$ |

Although the present invention has been shown and described with reference to particular examples, various changes and modifications which are obvious to persons skilled in the art to which the invention pertains are deemed to lie within the spirit, scope and contemplation of the subject matter set forth in the appended claims.

What is claimed is:

1. A composition of matter comprising: comprising a solvent; and an ester having a chemical structure chosen from (I), (II), or (III);

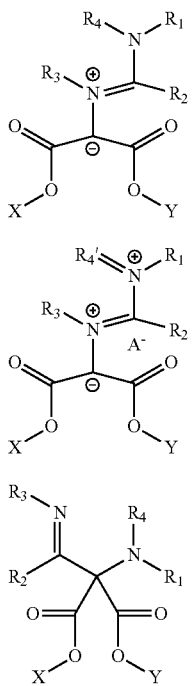

wherein X and Y are the same or different, wherein at least one of X and Y comprises an acid labile group, wherein $R_1$ is a saturated or unsaturated group having from 1-4 carbon atoms, $R_2$ is chosen from hydrogen or a saturated or unsaturated group having from 1-4 carbon atoms, $R_3$ is a saturated or unsaturated group having from 1-4 carbon atoms, and $R_4$ is a saturated or unsaturated group having from 1-4 carbon atoms, and $A^-$ is an anion.

2. The composition of matter of claim 1, wherein at least one of X or Y comprises a tert-butyl carbonate group.

3. The composition of matter of claim 1, wherein at least one of X or Y comprises

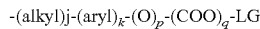

wherein i, j, k, p, and q take the values in the following table:

| -alkyl- j | -aryl- k | —O— p | —COO— q |
|---|---|---|---|
| 1 | 1 | 1 | 1 |
| 1 | 1 | 0 | 1 |
| 1 | 1 | 1 | 0 |
| 1 | 0 | 0 | 1 |
| 1 | 0 | 1 | 0 |
| 0 | 1 | 1 | 1 |
| 0 | 1 | 0 | 1 |
| 0 | 1 | 1 | 0 |
| 0 | 0 | 0 | 1 | wherein alkyl is a branched or unbranched, substituted or unsubstituted divalent alkyl chain of 1-16 carbon atoms having 0-16 heteroatoms substituted into the chain, aryl is a substituted or unsubstituted divalent phenyl group, divalent heteroaromatic group, or divalent fused aromatic or fused heteroaromatic group, and wherein LG is a leaving group.

4. The composition of matter of claim 3, wherein the leaving group is a tert-butyl group, a tert-pentyl group, a 2,3-dimethylbutan-2-yl group, a 2,3,3-trimethylbutan-2-yl group, a 2,3-dimethylpentan-3-yl group, a 2-methylbicyclo[2.2.1]heptan-2-yl group, a bicyclo[2.2.1]heptan-2-yl group, a 1-methylcyclopentyl group, a 1-ethylcyclopentyl group, a 1-methylcyclohexyl group, a 1-ethylcyclohexyl group, a 2-methyladamantyl group, or a 2-ethyladamantyl group.

5. The composition of matter of claim 1, further comprising, in admixture, one or more photoacid generators chosen from a sulfonium salt, an iodonium salt, a sulfone imide, a halogen-containing compound, a sulfone compound, an ester sulfonate compound, a diazomethane compound, a dicarboximidyl sulfonic acid ester, an ylideneaminooxy sulfonic acid ester, a sulfanyldiazomethane, or a mixture thereof.

6. The composition of matter of claim 5, further comprising at least one crosslinker, wherein the at least one crosslinker comprises an acid sensitive monomer or polymer, and wherein the at least one crosslinker comprises at least one of a glycidyl ether, glycidyl ester, glycidyl amine, a methoxymethyl group, an ethoxy methyl group, a butoxymethyl group, a benzyloxymethyl group, dimethylamino methyl group, diethylamino methyl group, a dibutoxymethyl group, a dimethylol amino methyl group, diethylol amino methyl group, a dibutylol amino methyl group, a morpholino methyl group, acetoxymethyl group, benzyloxy methyl group, formyl group, acetyl group, vinyl group, or an isopropenyl group.

7. The composition of matter of claim 6, wherein the at least one crosslinker comprises one or more glycidyl ether groups attached to a novolac resin.

8. A composition of matter comprising: a solvent; and an ester having a chemical structure chosen from (IV), (V), or (VI);

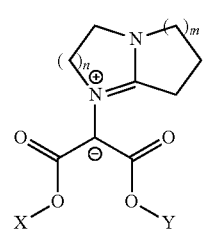

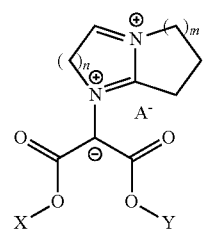

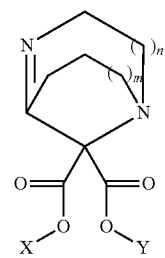

wherein m=1-4, n=1-4, and wherein X and Y are the same or different, wherein at least one of X and Y comprises an acid labile group, and wherein $A^-$ is an anion.

9. The composition of matter of claim 8, wherein at least one of X or Y comprises a tert-butylcarbonate group.

10. The composition of matter of claim 8, wherein at least one of X or Y has the structure -E-O$_p$-(COO)$_q$-LG wherein E is an optional extender group, LG is a leaving group and p and q take values chosen from the following table:

| (—E—)       | (—O—) | (—COO—) |
|-------------|-------|---------|
| Present     | p     | q       |
| Present     | 1     | 1       |
| Present     | 0     | 1       |
| Present     | 1     | 0       |
| Not Present | 0     | 1.      |

11. The composition of matter of claim 8, wherein LG is a tert-butyl group.

12. The composition of matter of claim 8, wherein LG is chosen from a tertiary alkyl or cycloalkyl group, a ketal or cyclic aliphatic ketal, or an acetal.

13. The composition of matter of claim 8, wherein at least one of X or Y comprises -(alkyl)j-(aryl)$_k$-(O)$_p$-(COO)$_q$-LG wherein j, k, p, and q take the values in the following table:

| -alkyl- j | -aryl- k | —O— p | —COO— q |
|-----------|----------|-------|---------|
| 1         | 1        | 1     | 1       |
| 1         | 1        | 0     | 1       |
| 1         | 1        | 1     | 0       |
| 1         | 0        | 0     | 1       |
| 1         | 0        | 1     | 0       |
| 0         | 1        | 1     | 1       |
| 0         | 1        | 0     | 1       |
| 0         | 1        | 1     | 0       |
| 0         | 0        | 0     | 1       | wherein alkyl is a branched or unbranched, substituted or unsubstituted divalent alkyl chain of 1-16 carbon atoms having 0-16 heteroatoms substituted into the chain, aryl is a substituted or unsubstituted divalent phenyl group, divalent heteroaromatic group, or divalent fused aromatic or fused heteroaromatic group, and wherein LG is a leaving group.

14. The composition of matter of claim 13, wherein m=2 and n=3, and wherein the leaving group is a tert-butyl group.

15. The composition of matter of claim 14, wherein LG is chosen from a tertiary alkyl or cycloalkyl group, a ketal or cyclic aliphatic ketal, or an acetal.

16. The composition of matter of claim 14, wherein LG is a tert-butyl group, a tert-pentyl group, a 2,3-dimethylbutan-2-yl group, a 2,3,3-trimethylbutan-2-yl group, a 2,3-dimethylpentan-3-yl group, a 2-methylbicyclo[2.2.1]heptan-2-yl group, a bicyclo[2.2.1]heptan-2-yl group, a 1-methylcyclopentyl group, a 1-ethylcyclopentyl group, a 1-methylcyclohexyl group, a 1-ethylcyclohexyl group, a 2-methyladamantyl group, or a 2-ethyladamantyl group.

17. The composition of matter of claim 14, further comprising, in admixture, one or more photoacid generators chosen from a sulfonium salt, an iodonium salt, a sulfone imide, a halogen-containing compound, a sulfone compound, an ester sulfonate compound, a diazomethane compound, a dicarboximidyl sulfonic acid ester, an ylideneaminooxy sulfonic acid ester, a sulfanyldiazomethane, or a mixture thereof.

18. The composition of matter of claim 8, further comprising, in admixture, one or more photoacid generators chosen from a sulfonium salt, an iodonium salt, a sulfone imide, a halogen-containing compound, a sulfone compound, an ester sulfonate compound, a diazomethane compound, a dicarboximidyl sulfonic acid ester, an ylideneaminooxy sulfonic acid ester, a sulfanyldiazomethane, or a mixture thereof.

19. The composition of matter of claim 18, further comprising at least one crosslinker, wherein the at least one crosslinker comprises an acid sensitive monomer or polymer, and wherein the at least one crosslinker comprises at least one of a glycidyl ether, glycidyl ester, glycidyl amine, a methoxymethyl group, an ethoxy methyl group, a butoxymethyl group, a benzyloxymethyl group, dimethylamino methyl group, diethylamino methyl group, a dibutoxymethyl group, a dimethylol amino methyl group, diethylol amino methyl group, a dibutylol amino methyl group, a morpholino methyl group, acetoxymethyl group, benzyloxy methyl group, formyl group, acetyl group, vinyl group, or an isopropenyl group.

20. The composition of matter of claim 18, wherein the at least one crosslinker comprises one or more glycidyl ether groups attached to a novolac resin.

* * * * *